United States Patent [19]

Matkovich

[11] Patent Number: 4,976,926
[45] Date of Patent: Dec. 11, 1990

[54] VACUUM DIAGNOSTIC DEVICE

[75] Inventor: Vlado I. Matkovich, Glen Cove, N.Y.

[73] Assignee: Pall Corporation, Glen Cove, N.Y.

[21] Appl. No.: 225,023

[22] Filed: Jul. 28, 1988

Related U.S. Application Data

[63] Continuation-in-part of Ser. No. 941,356, Dec. 15, 1986, Pat. No. 4,789,526.

[51] Int. Cl.⁵ .............................................. B01L 11/00
[52] U.S. Cl. ..................................... 422/101; 436/178
[58] Field of Search ................ 422/100, 101; 436/178, 436/180; 222/383, 390–392, 386; 73/864.02, 864.11, 864.14, 864.16, 864.18

[56] References Cited

U.S. PATENT DOCUMENTS

| 528,802 | 11/1894 | Pratt | 222/390 X |
|---|---|---|---|
| 857,547 | 6/1907 | Weber | 222/390 |
| 1,055,028 | 3/1913 | Flynn et al. | 222/390 X |
| 1,154,351 | 9/1915 | Tournadre | 222/390 |
| 1,286,875 | 12/1918 | Emerson | 222/390 X |
| 1,522,975 | 1/1925 | Phillips | 222/390 X |
| 2,595,493 | 5/1952 | Slaby et al. | 73/864.11 |
| 3,241,729 | 3/1966 | Gabler | 222/390 |
| 3,730,352 | 5/1973 | Cohen et al. | 422/102 X |
| 3,802,843 | 4/1974 | Kim | 23/259 |
| 3,815,787 | 6/1974 | Spies | 222/390 X |
| 3,838,978 | 10/1974 | Eddlemen et al. | 23/292 |
| 3,888,629 | 6/1975 | Bagshawe | 23/230 |
| 3,909,363 | 9/1975 | Bucalo | 422/61 X |
| 3,985,032 | 10/1976 | Avakian | 422/101 X |
| 4,014,653 | 3/1977 | Gianos et al. | 23/259 |
| 4,059,020 | 11/1977 | Avakian | 422/101 X |
| 4,138,474 | 2/1979 | Updike | 424/1 |
| 4,356,149 | 10/1982 | Kitajima et al. | 422/57 X |
| 4,789,526 | 12/1988 | Matkovich | 436/178 X |
| 4,797,260 | 1/1989 | Parker | 422/101 |

OTHER PUBLICATIONS

Literature-V-Tech, Inc. (Date Uncertain, Possibly, Jun. 1986).

Primary Examiner—Robert J. Hill, Jr.
Attorney, Agent, or Firm—Leydig, Voit & Mayer

[57] ABSTRACT

A diagnostic device is provided comprising a housing including a chamber having one portion open to the exterior of the housing and another portion which is closed to the exterior of the housing; a porous structure, such as a hydrophilic membrane, having at least one wettable layer, disposed across the open portion of the chamber and hermetically sealed to the housing; a valve in a wall of the housing; and a means for increasing the volume of the closed portion of the chamber to thereby decrease the pressure within the closed portion of the chamber such that after the wettable layer is wetted, the diagnostic device is capable of maintaining a pressure differential across the porous structure after the volume of the closed portion of the chamber has been increased by the volume increasing means to create a pressure differential across the porous structure.

8 Claims, 4 Drawing Sheets

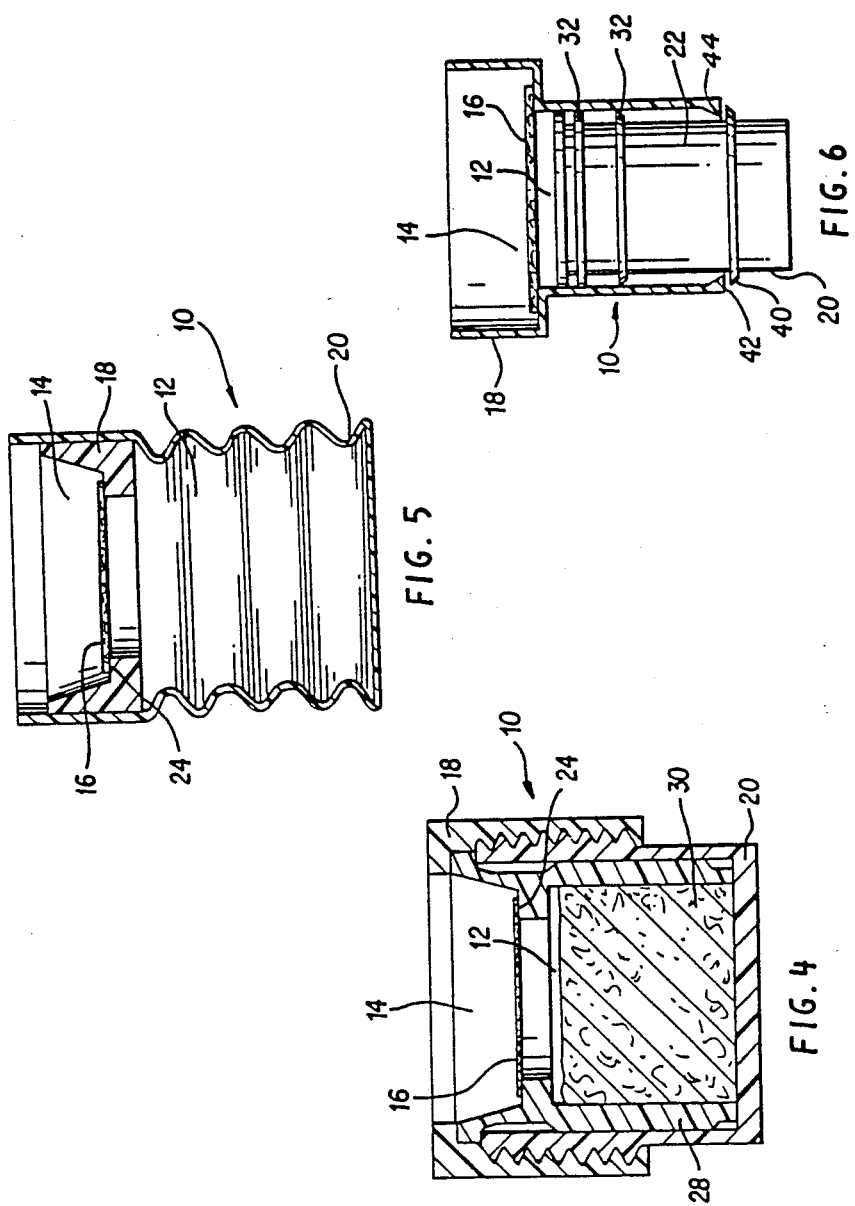

VACUUM DIAGNOSTIC DEVICE

This application is a continuation-in-part application of U.S. application Ser. No. 06/941,356, filed Dec. 15, 1986, now U.S. Pat. No. 4,789,526.

TECHNICAL FIELD

The present invention relates to diagnostic devices suitable for performing chemical and/or biological assays of a clinical nature. More particularly, the present invention is directed to diagnostic devices which include differential pressure means for removing an analyte-containing fluid from a test surface.

BACKGROUND ART

In contrast to the often elaborate analytical procedures and unwieldy, expensive equipment sometimes required in clinical diagnoses in the recent past, advances in medical research have led to the development of both of simpler procedures and equipment. Whereas previously employed techniques involved multiple steps and, in some cases, required both a high degree of dexterity and familiarity with the test procedures, kits and devices are now available which in some cases allow one with only limited laboratory experience to quickly and accurately perform diagnostic tests. Many of the techniques and devices provide an optical indication of a positive test, such as a color change, resulting from the reaction of (1) a substance being analyzed for (analyte), and (2) a test reagent or reagents. The analyte and/or test reagent may be a simple chemical substance or a more complex macromolecular substance from a biological fluid. The optical indication of the presence of the analyte may take place in solution, or on a solid surface, such as the interior surface of a glass or plastic tube, the well of a spot or a multiwell plate, or on a porous material such as a filter paper or membrane. Because of the typical white background of a porous material, a preference has existed for such materials in some instances and has also been incorporated in the form of porous membranes or matrices in test devices used alone or in specific test kits.

Typically, such devices locate the porous membrane in the bottom of a well adapted to receive the analyte-containing liquid. With the membrane treated with a test reagent or reagents prior or subsequent to introduction of the analyte-containing liquid to the well, the liquid passes through the membrane whereby sufficient analyte is specifically or nonspecifically adsorbed or retained on or within the membrane to undergo an optically indicating reaction with the test reagent(s). Typically, the liquid passes through the membrane due to gravitational forces, possibly assisted by a wicking or capillary action of an adsorbent material placed in contact with a surface of the porous membrane below or on the downstream side of the membrane.

Such means for removing liquid from a liquid analyte sample while retaining sufficient analyte on or within the membrane to perform tests on the analyte suffers from certain shortcomings. In some situations, the porous member exhibits a relatively low affinity for the analyte and is of a highly porous nature. Thus, the liquid sample containing the analyte passes through the porous member so rapidly that insufficient analyte is retained on or within the member to perform diagnostic tests. In other instances, passage of liquid through the member is too slow to make rapid diagnostic tests feasible. This has been the motivation for designing devices to increase the flow of analyte-containing fluid through the porous member. Although an improvement over gravity-induced passage of liquid, devices which employ an absorbent member in contact with the porous member to increase flow, are still too slow in many instances to provide satisfactory drainage from a porous member. This is particularly the case when the analyte-containing liquid is viscous or when, because of the analyte being tested for, a porous member with very small pores is required. The use of such devices thus limits the types of samples and analytes which may be tested. In some situations, although such devices provide adequate drainage rates, the flow through the porous member is uneven, due largely to air blockage below the porous member or non-linear capillary wicking into the adsorbent below.

There are some devices which provide adequate drainage rates by being connected to a source of differential pressure. Thus, variants of a suction flask and filter funnel have been used to obtain more rapid drainage or flow rates and, concomitantly, more rapid test results. However, such devices require differential pressure sources, such as a vacuum pump or an aspirator line. Such means for providing a differential pressure across the porous member, while effective in improving drainage rates or flow through the porous member, are not always available and, when available, are sometimes difficult to adjust or control the vacuum (differential pressure) generated.

For the reasons discussed above, there is a need for a device which provides not only a suitable porous member to permit retention of an analyte and test reagents but which also is operatively associated with a means for providing a rapid, but controlled, passage of liquid through the porous member. Preferably, the device should contain the means for providing a rapid and uniform passage of liquid through the porous member in a single, self-contained unit.

DISCLOSURE OF THE INVENTION

The present invention is directed to a diagnostic device, which in a single unit provides a porous structure or member that by proper selection is capable of retaining an analyte of a chemical or biological nature. The device is also capable, under specified conditions, of preventing the passage of fluids, both gaseous and liquid, across or through the porous structure for periods of time sufficient to permit adequate reaction of an analyte and a test reagent. The present invention also includes a means to provide rapid drainage or passage of fluid through the porous structure.

The diagnostic device of the present invention may be generally described as comprising a housing which includes a chamber having one portion thereof open to the exterior of the housing and another portion which is closed to the exterior of the housing. A porous structure is disposed across or athwart the open portion of the chamber and is hermetically sealed to the housing. The porous structure has a first surface which communicates with the exterior of the housing and a second surface which communicates with the closed portion of the chamber. The porous structure also includes at least one layer which is wettable by a liquid. To provide adequate flow or drainage rates of liquid across the wettable portion of the membrane, a means for decreasing the pressure within the closed portion of the chamber is provided. The bubble point of the wettable layer is chosen so as to be sufficient to maintain the desired pressure differential across the porous structure.

The devices of the present invention may be used to perform diagnostic tests by placing a liquid, particularly a liquid containing an analyte, on the first surface of the porous structure. After the wettable layer is wetted, the pressure in the closed portion of the chamber, i.e., within the chamber, is decreased so that a major portion or excess of the fluid is drawn through the porous structure into the closed portion, i.e., the interior of the chamber. Because of the bubble point characteristics of the porous structure and the hermetic seal of the porous structure across or athwart the open portion of the chamber, a decreased pressure in the closed portion of the chamber can be maintained.

The means for decreasing the pressure within the closed portion of the chamber typically includes means for increasing the volume of the chamber, as by providing a movable side wall portion and/or bottom wall portion. Thus, the movable wall portion and/or bottom portion, in moving from a first position to a second position increases the volume of the chamber and thereby provides a pressure differential across the membrane which induces flow of liquid to the closed portion of the chamber.

The housing may also include valve means for providing fluid communication between the closed portion of the chamber and the atmosphere. Such valve means permits equilibration of pressure useful in some procedures and/or removal of liquid from the closed portion of the chamber.

BRIEF DESCRIPTION OF THE DRAWINGS

FIG. 4 illustrates an embodiment similar to that in FIG. 3, additionally containing an absorbent pad disposed within the chamber of the device.

FIG. 5 illustrates an embodiment of the invention employing a bellows structure to generate a partial vacuum.

FIG. 6 illustrates another embodiment of the present invention with a manually-operated piston.

BEST MODES FOR CARRYING OUT THE INVENTION

Figure 3:
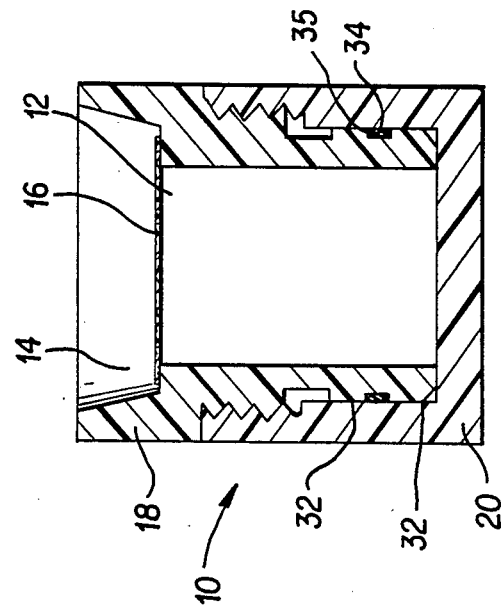
FIG. 3 illustrates another embodiment of the present invention in which a bottom wall of the chamber is movable with respect to the porous structure.

The devices according to the present invention may take a variety of forms. The particular devices illustrated in the drawings and described herein are intended to be illustrative and should not be construed as limiting the scope of the invention to the embodiments illustrated and described.

The same reference numerals are used in the drawings and herein to describe common elements found in each of the illustrated embodiments.

Examination of FIGS. 1 to 5 reveals that each of the embodiments includes a housing, indicated generally as 10, having a chamber 12 located therein. The housing 10 is also provided with an opening 14 in the upper portion thereof. Each of the devices includes a porous structure or membrane 16 disposed across or athwart the opening 14 and hermetically sealed to the interior surface of an upper or first housing section or member 18 of the housing 10. The sealing of the porous structure or membrane to the upper or first housing member can be accomplished by the application of heat either directly in the form of radiant heat by a heater block or as ultrasonic energy using a welding horn. In this manner, the porous structure or membrane is sealed to the edges of the upper housing. Secured to and movable with respect to the upper housing section 18 is a lower or second housing section or member 20.

The housing, and particularly the section of housing which is in contact with the porous member, may suitably be formed from any material which is chemically inert toward substances with which it comes in contact during the diagnostic test. Preferably, the material used for the upper section of the housing is also capable of forming a heat seal with the material used to form the porous structure. In the embodiments illustrated in FIGS. 1 to 4, 6, and 7, it is also preferred that slidable contacting surfaces be self-sealing. Suitable materials from which the housing may be formed include plastics such as polystyrenes, polyolefins, such as polyethylene and polypropylene, and rubber-like materials such as Kraton ®, a styrene-butadiene elastomer available from Shell Chemical Company.

The porous structure or membrane 16 employed in the present invention has characteristics which, in combination with appropriate sealing means, impart the unique ability of the devices in accordance with the present invention to maintain a reduced pressure within the chamber for protracted periods of time despite the relatively small volume of the chamber and the small size of the devices as a whole.

The porous structure 16 includes at least one layer of a material wettable by, or liquophilic, preferably hydrophilic, with regard to, the test liquid(s). The wettability or liquophilicity of a solid structure, e.g., a membrane, is a function of that structure's critical surface energy and the surface tension of the applied liquid. If the critical surface energy is at least as high as the surface tension of the liquid, the liquid will spontaneously wet the solid structure. For example, a porous membrane having a critical surface energy of 72 dynes/cm or higher will be wetted by water which has a surface tension of 72 dynes/cm and, therefore, tend to freely pass aqueous solutions, i.e., the membrane is hydrophilic. The capability of a porous structure (membrane) to be wetted by a liquid can be determined by placing a drop of the liquid on the porous structure. The angle of contact provides a quantitative measure of wetting. A very high angle of contact indicates poor wetting and may be used to characterize a "liquophobic" material, while a zero angle of contact defines complete or perfect wetting. Materials used in the subject invention as the wettable or liquophilic porous layer are characterized by being readily or spontaneously wetted by the applied liquid and have a low angle of contact with the applied liquid. Indeed, when a drop of a test liquid(s) is placed on the wettable or liquiphilic layer of the porous structure 16, the drop of liquid penetrates the layer and provides a low angle of contact with the first or upper surface of the porous structure.

In addition to having one layer which is liquophilic or wettable by the test liquid(s), the porous structure has preferred pore dimensions which would generally be characterized as microporous. Thus, the material from which the porous structure is formed has an absolute pore rating suitably between about 0.04 and about 5 microns, preferably about 0.1 to about 3 microns and most preferably about 0.45 to about 1.2 microns. Suitable materials for the porous structure 16 should also be inert toward substances encountered in any step of the diagnostic test. This includes analytes, reagents employed and liquids which form the fluid medium for either the analyte or a reagent.

As used herein, analyte refers to any substance or substances being analyzed for or determined by the diagnostic test. The term "reagent" and like terms refer both to substances reacting directly with an analyte as well as to substances used to convert either another substance or the analyte to a substance suitable for providing an indication, typically an optical indication, of the presence of the analyte. The term includes simple chemical substances, including elements and compounds, of an ionic or molecular nature as well as more complex or macromolecular structures, such as proteinaceous materials, and includes substances of a biological nature such as antigens, antibodies, enzymes, antibody-enzyme conjugates, haptens, receptors, lectins, gene probes, and the like, as well as viruses and bacteria. The analyte may also be one or more of the substances falling within the definition of a reagent. In the case of antibodies, reagents and analytes may each be monoclonal or polyclonal antibodies. Additionally, the analyte may include drugs, peptides, cells, and organelles. A reagent may additionally include buffers, indicator molecules, and substrates.

A suitable porous structure, while being chemically inert toward the aforementioned substances, may have some affinity for the analyte and selective affinity for a reagent. In some instances, it is preferred that the wettable membrane be pretreated with a reagent, that is, treated with a reagent prior to addition of an analyte-containing liquid. Typically this would include pre-treatment of the wettable layer before or after assembly of the diagnostic device, but prior to shipment to a user of the device. In this manner, the devices of the present invention could be supplied as a kit for a specific test, incorporating in the porous structure some or all of the necessary reagent(s) and possibly supplied with such other reagents to be added to the porous structure as the test requires.

Examples of materials which are suitable for use as the wettable layer of the present invention include microporous, hydrophilic membranes including polyamides, polyvinylidene fluoride, nitrocellulose, and mixed esters of nitrocellulose. Hydrophilic, microporous polyamide membranes, particularly nylon 66, are particularly preferred.

A preferred microporous, hydrophilic nylon 66 membrane material having high binding capacity, uniformity, controlled pore size and high surface area is BIO-DYNE® available from Pall Corporation (see U.S. Pat. No. 4,340,479 which is incorporated herein by reference).

Another preferred membrane useful as the indicator medium or test field is IMMUNODYNE TM available from Pall Corporation. IMMUNODYNE TM is a modified CARBOXYDYNE® membrane, also available from Pall Corporation. CARBOXYDYNE® is a hydrophilic, microporous, skinless nylon 66 membrane with controlled surface properties formed by the co-casting process described in U.S. patent application Ser. No. 850,061, as discussed below, specifically by cocasting nylon 66 and a polymer containing an abundance of carboxyl groups to form a membrane having controlled surface properties characterized by carboxyl functional groups at its surfaces. IMMUNODYNE TM membranes may be prepared from CARBOXYDYNE® membranes by treating them with trichloro-s-triazine in the manner described in U.S. patent application Ser. No. 642,899, discussed below.

Polyvinylidene fluoride membranes are not inherently water-wettable but can be rendered such by an appropriate surface treatment. Microporous, polyvinylidene fluoride membranes which have been treated to render them hydrophilic are commercially available. As discussed above, wettability or liquophilicity is a function of the critical surface energy of the solid structure and the surface tension of the liquid. Wettability may also be expressed in terms of intrusion pressure required for liquid to penetrate into the pores of the membrane. Although a function of the properties of the liquid used, such as surface tension, membrane materials which are particularly preferred have intrusion pressures of, or close to, zero.

Membranes useful as the porous structure in the subject invention typically have large surface areas, e.g., from about 2 to about 10 $m^2$/gram or even higher. As employed herein, the term "surface area" refers not only to the gross surface(s) of the porous structure but also to the surfaces of the micropores, i.e., the interior surfaces of the structure which are contacted by fluid during use. This characteristic permits a greater amount or higher concentration of reactant to be immobilized in the indicator medium. Accordingly, higher sensitivities may be achieved using the diagnostic device in accordance with the present invention.

Also included among the preferred polyamide membranes for the present invention are hydrophilic, microporous, skinless polyamide membranes with controlled surface properties of the type described in (1) U.S. patent application Ser. No. 850,061, filed Apr. 7, 1986, which is a continuation application of U.S. patent application Ser. No. 459,956, filed Jan. 21, 1983, which in turn is a continuation-in-part application of U.S. patent application Ser. No. 346,118, filed Feb. 5, 1982, and in (2) U.S. patent application Ser. No. 848,911, filed Apr. 7, 1986, which is a continuation application of U.S. patent application Ser. No. 460,019, filed Jan. 2, 1983, which is a continuation-in-part application of U.S. patent application Ser. No. 346,119, filed Feb. 5, 1982. All of the aforementioned U.S. patent applications are specifically incorporated herein by reference. These hydrophilic, microporous, substantially alcohol-insoluble polyamide membranes with controlled surface properties are formed by cocasting an alcohol-insoluble polyamide resin with a water-soluble, membrane-surface-modifying polymer having functional polar groups. Like the preferred hydrophilic, microporous nylon membranes which do not have controlled surface-modified polar groups present, the polyamide membranes used as the indicator medium or test field in the present invention having controlled surface properties are also skinless; that is, they are characterized by through pores extending from surface to surface which are of substantially uniform size and shape. If desired, however, materials having tapered through pores, i.e., pores which are larger at one surface of the sheet, narrowing as they approach the opposite surface of the sheet, may be used.

The surface-modifying polymers used to prepare the polyamide membranes with controlled surface properties, useful in the present invention, comprise polymers which contain substantial proportions of chemical functional groups, such as hydroxyl, carboxyl, amine, and imine groups. As a result, the membranes include, at their surfaces, high concentrations of functional groups such as hydroxyl, carboxyl, imine, or a combination of any of the above groups which do not react with one another. These polyamide membranes having controlled surface properties have higher concentrations of carboxyl or imine groups at their surfaces than the preferred microporous, hydrophilic, skinless polyamide membranes described above which do not have controlled surface properties, i.e., those which are formed from the preferred polyamide resin but are not cocast with surface-modifying polymer.

The membranes used may be treated by any method known to one of skill in the art to deposit and/or bind reagents thereto. As indicated above, the reagent may be of an ionic, molecular, or macromolecular nature. When used as a diagnostic tool to provide a visible change, the reagent may be one or a combination of substances which is initially colorless and which, upon reaction with a suitable material, provides an optically measurable response. Other possible variations include the use of suitable labels, such as the formation between the deposited reagent and the material for which testing is being conducted of a complex or compound which is appropriately labeled by any known technique, such as enzymatic/substrate labels or the like.

Although treatment of the porous structure or membrane of the diagnostic device with a suitable reagent(s) may be performed at the time at which diagnostic tests are to be performed, specifically by addition of the test reagent(s) immediately preceding contacting of the test device with the liquid containing the sample to be analyzed for, the present invention may have application to a diagnostic device prepared by treatment of the membrane with the test reagent(s) prior to the manufacture of the individual diagnostic devices.

A useful method of binding reagents of a molecular nature, especially macromolecules, and particularly those of a biological nature, is disclosed in U.S. patent application Ser. No. 642,899, filed Aug. 21, 1984, and specifically incorporated herein by reference. This application describes a method for immobilizing a wide range of biologically active substances as acceptor molecules on active membranes. The acceptor-bound membranes described in the application are capable of immobilizing and binding a wide variety of biologically-active compounds, specifically ligands, to the acceptor molecules. Using such reaction layers or membranes in the porous structure permits the testing of bodily fluids, such as blood, serum, plasma, urine, saliva, and the like. Use of such membranes also permits testing for particular substances by chemical assays or immunoassays, such as those where a specific label is employed, such as one indicating enzyme activity or an electromagnetic energy absorbing and/or emitting label, such as a fluoroescent label. The macromolecules used as reagents and bound to the surfaces of the microporous membrane or which are assayed for using the device of the present invention generally include materials of a biological nature and are frequently proteinaceous in nature. The reagent or acceptor molecule bound directly to the reaction layer or the ligand being tested for include immunoglobulins or antibodies, either polyclonal or monoclonal, antigenic substances, apoproteins, receptors, glycoproteins, lectins, carbohydrates, hormones, enzymes, carrier proteins, heparin, coagulation factors, enzyme substrates, inhibitors, cofactors, nucleic acids, etc.

In many instances, it is preferred that the porous structure 16 include only a single layer, the wettable layer discussed above. However, in some instances, it is preferred to employ a composite structure including at least the wettable layer and one or more other layers. Thus, when only a wettable layer is employed, liquid placed on the layer will wet the layer on contact therewith. Rapid passage of the liquid through the layer will not normally occur until a pressure differential across the layer is established, such as when a decreased pressure is formed within the device, as described below. However, slow seepage of liquid through the layer due to gravity may occur in some instances.

When a reaction between an analyte and a reagent occurs in the porous structure which is rapid, such as when the wettable or reaction layer which has been pretreated with a reagent contacts an analyte-containing liquid, such seepage may be acceptable. However, in those instances in which the reaction rate of an analyte with a reagent or with a first reagent is slow, or a long lag time is required before reaction is substantially complete, it may be desirable to maintain the analyte-containing liquid in contact with the wettable reaction layer for a longer period of time. In such instances, it is desirable to prevent seepage of the analyte-containing liquid through the wettable layer. One method for reducing or eliminating such seepage is to place a second layer of a liquophobic material below, preferably in intimate contact with, or, most preferably, bonded to the downstream side, i.e., the side facing the closed portion of the chamber, of the wettable layer. The term "liquophobic" as used herein is effectively the obverse of the term "liquophilic". That is, a liquophobic material has a critical surface energy lower than the surface tension of the applied liquid and is not readily or spontaneously wetted by the applied liquid(s). Liquophobic materials then are characterized by a high contact angle between a drop of liquid placed on the surface and the surface. Such a high contact angle indicates poor wetting. By using a liquophobic or non-wetting layer, the first liquid to be applied to the upstream side of the wettable layer, i.e., facing the exterior of the device, does not pass through the porous structure and into the chamber until a decreased pressure is established within the chamber.

Materials suitable for use as the liquophobic layer include polymeric halocarbons, such as polyvinyl chloride, polyvinylidene difluoride, polytetrafluoroethylene, etc., and polyolefins, such as polyethylene and polypropylene. A preferred material is a synthetic thermoplastic polymeric web of microfibers, and in particular, polypropylene microfibers. When a liquophobic layer is used in combination with a liquophilic microporous membrane, the preferred structure is a composite of the two layers in which the synthetic thermoplastic polymeric web of microfibers is secured to the membrane without the use of added adhesive components.

When the analyte constitutes a bacteria or other particulate analyte, or a particulate reagent or reagent-/analyte complex, such as coated latex beads, the wettable layer of the porous structure may not provide an adequate capacity to retain all the bacteria in the sample specimen or a suitable surface from which an optical indication of the presence of an analyte may be viewed. In such a situation, it is preferred to place on the upstream side of the wettable layer a prefilter, such as a porous depth filter layer, preferably a glass or polypropylene fiber layer, which is capable of retaining bacteria thereon. The depth filter layer is placed upstream, preferably in intimate contact with, or, more preferably, bonded to the wettable layer of the porous structure.

As indicated above, the retention of a decreased pressure within the chamber for an extended period of time requires that the device of the present invention include several features. The first of these is the requirement that the bubble point of the wettable layer of the porous structure 16 be sufficient to maintain the pressure differential across the porous structure. This includes uniformity of the pores as well as a pore size below about 5 microns, preferably below about 3 microns. The term "bubble point" as used herein refers to the pressure at which air or gas flow through the wetted membrane increases very sharply, i.e., the point at which the wetting liquid is blown out of the pores of the structure under the applied pressure allowing rapid air flow through the membrane. The bubble point is a function of the pore size, i.e., liquid in large pores is more readily displaced under an applied differential pressure, allowing free air flow. Wettable layers having uniform pore sizes are preferred since more uniform flow of liquid through the membrane and concomitant uniform laydown of analyte results.

The second requirement for maintaining a decreased pressure within the chamber of the device is a fluid-impervious or hermetic seal formed between the walls of the upper portion 18 of the housing 10 and the porous structure 16. Any known technique for forming the hermetic seal may be employed. Preferred is a heat-sealing technique which bonds the material of the porous structure to the walls of the housing. When a layer of hydrophobic material and/or depth filter is employed with the wettable layer, bonding of the latter to either of the other materials and to the walls of the housing may be accomplished in a single heat-sealing step.

Figure 2:
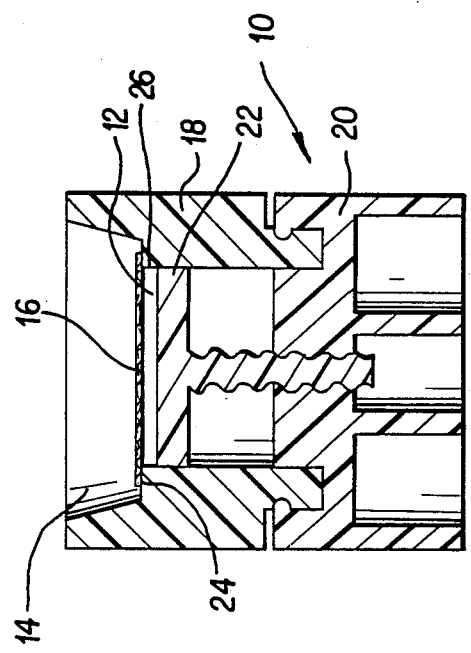
FIG. 2 illustrates another embodiment of the present invention similar to that shown in FIG. 1.
Figure 1:
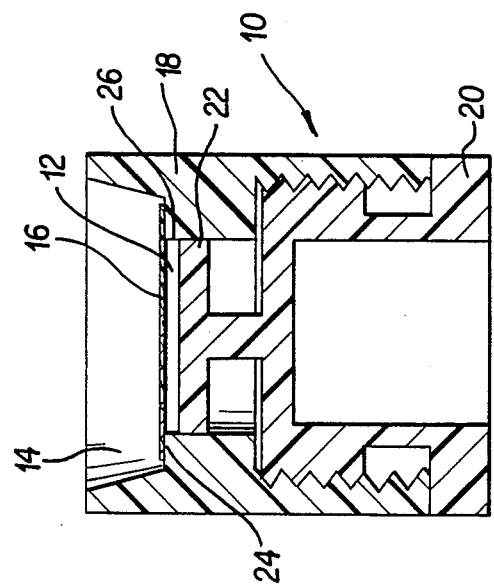
FIG. 1 illustrates an embodiment of the present invention employing a piston movable within a bore to generate a partial vacuum.

The third requirement for maintaining a decreased pressure within the chamber of the devices according to the present invention is adequate sealing means, particularly gaseous sealing means, between the upper and lower housing portions, 18 and 20. Sealing may be achieved by using very tight tolerances between slidable contacting surfaces of the upper and lower housing sections. Depending on the choice of material, those materials which are somewhat compressible will permit adequate sealing in most situations. When devices such as those illustrated in FIGS. 1 and 2 are employed, the piston 22 may have a flange formed on the peripheral contacting surface to allow sealing engagement with the walls of the chamber. Other sealing means, such as O-rings, may be employed at various locations in each device. These will be discussed in greater detail in the discussion of individual devices.

A first preferred embodiment of the present invention is illustrated in FIG. 1. As in most of the preferred embodiments of the invention, the porous structure 16 is placed in the opening 14 of the chamber 12 and is preferably recessed from the mouth of the opening by a sufficient amount to provide a well in the opening for receiving liquids. As illustrated in FIG. 1, the diameter of the wall of the opening below the porous structure is preferably narrower than above the porous structure, forming a shoulder portion 24 to which the porous structure is sealed by suitable means, such as by heat sealing.

The first or upper section of the housing 18 includes a bore 26 which defines the side walls of the chamber. The second or lower housing portion 20 includes a plunger or piston 22 which, in the embodiment of FIG. 1, is non-rotatable with respect to the lower housing portion. Preferably, the piston is formed integrally with the lower housing section as a single unit. Each of the upper and lower housing sections is provided with a threaded section so that the two sections may threadedly and rotatably engage one another. Rotation of one of the upper or lower housing sections 18 or 20 with respect to the other housing section provides axial movement of the piston 22 within the bore. Thus, the upper surface of the piston may be considered to form a bottom wall of the chamber which, in combination with the side walls formed by the bore 26 and the underside or downstream side of the porous structure 16, defines the chamber 12 within the housing. In rotating one of the upper or lower housing sections, the piston 22 may be lowered within the bore 26 and, as the volume of the chamber increases, the pressure within the chamber decreases below that of the pressure on the exterior surface of the porous structure. In such manner, there is provided a pressure differential (vacuum) by which liquid which has wet the porous structure and lies above the porous structure is pulled through the porous structure into the chamber below.

The preferred embodiment illustrated in FIG. 2 is in many respects similar to that shown in FIG. 1. Thus, the embodiment shown in FIG. 2 also includes a plunger 22 which moves axially in a bore 26 in the upper housing section 18. However, unlike the embodiment of FIG. 1, the device shown in FIG. 2 employs a lower housing section 20 which is not threadedly joined to the upper housing section 18, but rather the two sections are rotatably joined to one another but do not permit axial movement of one with respect to the other when one of the sections is rotated with respect to the other.

The rotatable engagement may be accomplished by a tongue and groove arrangement, such as that illustrated in FIG. 2, or any other suitable arrangement which accomplishes such purpose. By comparison with the embodiment illustrated in FIG. 1, a further distinction exists with respect to the manner in which the piston or plunger is joined to and moves within the housing sections 18 and 20. Thus, in the embodiment of FIG. 1, the piston is fixedly arranged with respect to the lower housing section 20 such that the motion of the piston with respect to the lower housing section is fixed in an axial direction, being non-rotatable therewith, while being rotatable with respect to the upper housing section 18. However, in the embodiment of FIG. 2, the base or stem of the piston is provided with threads which engage corresponding threads in the lower housing section. The piston is also provided with a means to prevent rotation within the upper housing section, such as by employing a key either on one of an internal surface of the bore or the peripheral surface of the piston and a keyway on the other of the surfaces. Alternatively, a non-circular piston, e.g., a square piston, and commensurately shaped bore may be employed.

In the embodiment of FIG. 2, when one of the upper and lower housing sections is rotated with respect to the other, the piston moves in an axial direction but does not rotate with respect to the upper housing section.

The devices illustrated in FIGS. 3, 4, and 5, like those shown in FIGS. 1 and 2, also achieve a decreased pressure within the chamber 12 by increasing the volume of the chamber. However, they do not employ a movable piston within the chamber to serve as the bottom or enclosed end wall of the chamber. Rather, the embodiments shown in FIGS. 3 and 4 employ rigid housing portions 18 and 20 which threadedly engage one another. The embodiment illustrated in FIG. 5 differs from those of FIGS. 1–4 in that the lower housing section 20 is flexible, preferably in the form of a bellows. In addition, in the embodiment of FIG. 5, there are no movable surfaces where a sealing means is required.

In the embodiment shown in FIG. 3, the lower housing section 20 is provided with internal threads which threadedly engage external threads on the upper housing section 18. However, the threading on the upper and lower housing sections may be reversed with the lower housing section being provided with external threads and the upper housing section being provided with internal threads, and the lower housing section nesting in the upper, as in the embodiment shown in FIG. 4.

The device illustrated in FIG. 4 includes an additional housing member or sleeve 28 within the upper and lower housing sections 18 and 20 and an absorbent pad 30 within the chamber 12. The sleeve 28, which preferably has the porous structure 16 secured to a shoulder 24, is fixed to the upper housing member 18. Depending on the materials employed to form the housing components and the manufacturing techniques employed, it may be preferable to form the upper housing section 18 and the sleeve 28 as a single unit. In use, the absorbent pad 30 is held tightly within the chamber 12, spaced from the porous structure 16. As the upper and lower housing sections 18 and 20 are rotated with respect to one another, the distance between the porous structure 16 and the upper surface of the absorbent pad 30 remains substantially constant while a space of increased volume is created between the internal surface of the bottom wall of the lower housing section 20 and the bottom surface of the absorbent pad 30. Since the absorbent pad is preferably formed from a highly porous material having a large voids volume, such as cellulose acetate, as the housing sections are unthreaded, the decreased pressure established within the chamber 12 rapidly equilibrates. Although a device having an absorbent pad is illustrated in the embodiment of FIG. 4 which includes an internal sleeve 28, other embodiments, such as the device shown in FIG. 3, may also be provided with an absorbent pad.

Figure 7:
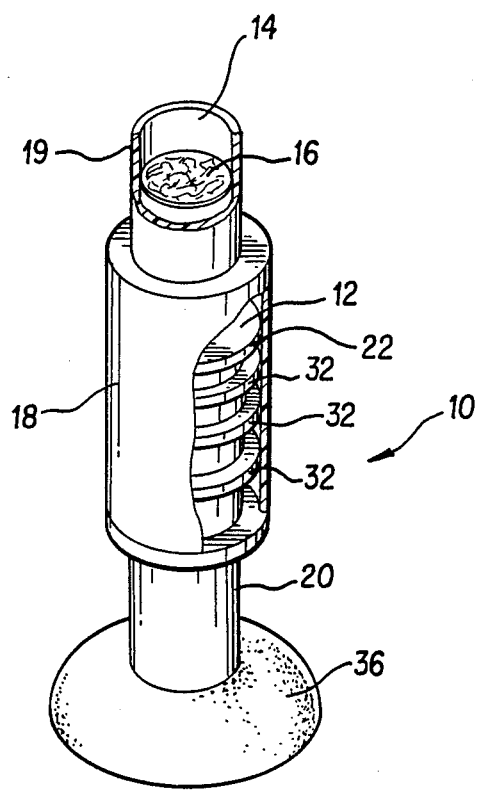
FIG. 7 illustrates a further embodiment of the invention including a piston and a means for detachably securing the device to a stationary object.

FIGS. 6 and 7 illustrate embodiments similar to those shown in FIGS. 1 and 2. Thus, both include pistons 22 movable with respect to and axially slidable within a bore in an upper housing section 18. The piston may also be considered to serve as a lower section of the housing 20 and form a movable bottom or end wall of the chamber 12. However, unlike the embodiments illustrated in FIGS. 1 and 2, neither the piston 22 nor the lower housing section 20 threadedly engages another element of the device. Rather, the volume of the chamber 12 is increased by pulling the upper and lower housing sections apart, that is, withdrawing the piston from the upper housing section 18. This may be done manually with the device illustrated in FIG. 6 by grasping the lower portion of the piston, i.e., the lower housing section 20, to withdraw the plunger or piston 22 from the upper housing section 18. The device illustrated in FIG. 7, however, includes a means for securing the lower housing section to a stationary object, such as a suction cup 36.

The embodiment illustrated in FIG. 7 also differs from the other embodiments in that the portion of the housing 18, identified as the porous structure retaining member 19, may be formed as part of the upper housing section 18 or, alternatively, may be a detachable member. Thus, the device allows the portion of the housing which contains the porous structure to be removed and disposed of after a test is performed. Another porous structure-retaining member 19 may then be placed on the upper housing section. The porous structure retaining member may be secured to the upper housing section by any convenient means, such as threading a bayonet insert, or some form of engaging locking means. Preferably, a means for fluid sealing, such as a gasket (not shown), is included between the housing 18 and the porous structure retaining member 19.

The embodiments shown in FIGS. 6 and 7 may be provided with a stop in any convenient form to prevent the piston 22 from contacting the porous structure 16 and possibly accidentally damaging the structure. The stop, shown in FIG. 6, comprises an annular outward projection 40 which, in a "closed" position of the piston 22, contacts the bottom 42 and, in particular, an inwardly projecting lip or flange 44 of the bottom 42 of the upper housing section 18. Alternatives to the annular outward projection 40 may be substituted, such as a pin or the like. Likewise, the embodiment shown in FIG. 2 may be provided with a stop to prevent damage to the porous structure 16.

To provide the third major requirement of adequate sealing in order to establish and maintain a decreased pressure within the chamber 12, sealing means are used between slidable contacting surfaces, such as the internal and external contacting surfaces of the upper and lower housing sections (FIGS. 3 and 4) or the peripheral surface of a piston and the internal wall of the upper housing section (FIGS. 1 and 2). The sealing means may simply be formed in a certain configuration on one of the slidable contacting surfaces from the material from which the member is formed. Thus, as shown best in FIG. 3, the external slidable contacting surface of the upper housing section 18 is provided with several, in this instance two, annular projections 32, preferably having a triangular or rectangular cross-section, which contact the inner slidable surface of the lower housing section 20. In addition, or as an alternative, to forming the sealing means in the slidable surface of the member itself, an annular member, such as an O-ring 34, may be placed in an annular groove 35 formed in the slidable surface of one of the members. In the embodiments shown in FIGS. 6 and 7, annular sealing means in the form of annular flanges 32 are located on the piston 22. These are represented as both annular projections or ribs 32. However, the sealing means may be an O-ring 34 in an annular groove(s) such as that shown in FIG. 3.

In operation, a small volume of liquid, either containing analyte, or, in some instances, a reagent, is introduced into the well above the outer surface or first surface of the porous member 16. Upon contact with the liquid, the porous member is wetted. When a long period of time is required for reaction between a component (analyte or reagent) of the first-added liquid and a reagent in the porous structure, the structure includes a liquophobic layer in intimate contact with or bonded to the downstream surface of the wettable layer. This prevents slow seepage of liquid through the porous structure to the chamber when there is no pressure differential across the porous structure. When it is desired to draw the liquid in contact with the porous structure into the chamber, the device is manipulated to increase the volume of the chamber, thereby forming a pressure differential across the porous structure, and cause the liquid to flow into the chamber. Unless such a large volume of liquid is employed in the first aliquot of liquid so as to fill a substantial portion of the chamber and increase the pressure within the chamber to about that of the ambient pressure above the porous structure, liquid which is added in subsequent aliquots will also pass rapidly through the porous structure because the pressure differential is maintained by virtue of the wetted layer, precluding entry of air into the closed chamber.

If it is desirable to reduce the flow rate of additional liquid aliquots through the porous structure, the pressure within the closed chamber can be increased to reduce or eliminate the pressure differential. By careful manipulation, it is possible to slowly reduce the volume of the chamber and thereby increase the pressure therein.

Alternatively, a pressure release valve may be incorporated into the housing. With such a device, the valve is opened and the pressure within the chamber is equilibrated with the external pressure.

Figure 8:
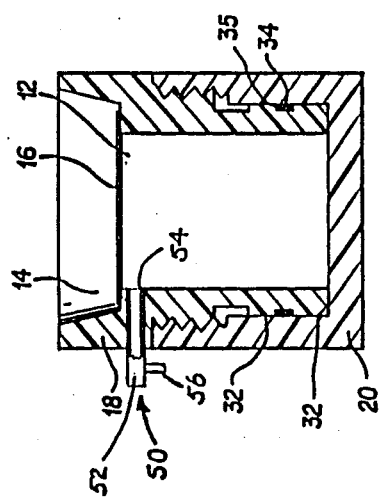
FIG. 8 illustrates an embodiment of the invention including a valve means.
Figure 9:
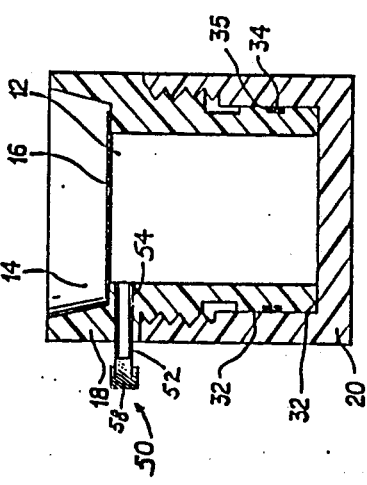
FIG. 9 illustrates an embodiment of the present invention which includes a different sort of valve than that shown in FIG. 8.

Examples of the types of pressure equilibrating valves which may be used in the present invention include plastic disposable 2- or 3-way valves, such as stopcocks having a built-in handle or lever. An example of such a device is illustrated in FIG. 8. As shown, the device having a 2-way valve, indicated generally as valve means 50, includes a tube 52 located within a port 54 which passes through the wall of the upper housing section 18. To operate the valve, the lever can be rotated to select either a closed or open position in which communication between the closed chamber and the exterior of the diagnostic device is either blocked or established, respectively. FIG. 9 illustrates an embodiment of the present invention which employs a more preferred type of valve means. The device also includes a port or duct 54 extending between the closed chamber and the exterior of the diagnostic device, and a closure member 58, such as a cap or plug, to block the port. This type of valve means is preferred because it is simpler and easier to manufacture than the 2-or 3-way valve described above. In a preferred form of the embodiment, the port includes a tube 52 passing through the upper portion 18 of the housing 10 and projecting outwardly from the housing or it may be simply an opening in the wall of the upper portion 18. The closure member may also take a variety of forms. The member may be a simple cap surrounding and fitting over the open end of the projecting tube or it may be a rod shaped male member or plug which is inserted within the opening of the duct 54 or tube 52. The plug or cap may simply be pressed into place or may be formed from a hard substance and may engage, such as by threading, the outer surface when in the form of a cap or the inner surface when in the form of a rod shaped plug. Alternatively, the closure member, whether a cap or plug, may be formed from an elastomeric material which because of its properties forms an adequate seal with the internal or external surface of the port. When the closure member is a plug, it may be in the form of a tapered rod of a somewhat compressible material which assures a satisfactory seal in the port. When an elastomeric member is employed, the closure member may be removed entirely from the port or fluid communication between the closed chamber and the exterior of the diagnostic device may be achieved by squeezing or manipulating the closure member so as to distort its shape and form a fluid passage. An alternate embodiment of the valve provides an elastomeric cap over the projecting end of the tube. The portion of the cap which lies over the open end of the tube is provided with a slit. When undisturbed, the slit adequately seals the open end of the tube but when the cap is squeezed the slit opens to allow fluid to pass therethrough.

Figure 10:
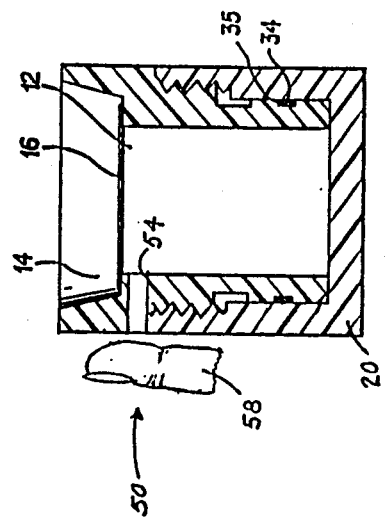
FIG. 10 illustrates still another embodiment of the invention which includes a valve means.

The most preferred embodiment of the valve means employed in the present invention, particularly from the aspect of simplicity and ease of manufacture, employs a port or duct 54 passing through the upper portion 18 of the housing 10. In this respect, this embodiment is similar to the one shown in FIG. 9 and described immediately above. However, rather than employing a closure member which is a cap fitting over the open outer end of a projecting tube or a plug inserted within the port, this embodiment merely employs as a closure member an object which sealingly covers the port formed in the wall of the housing. Such an object may take various forms, for example, a piece of sealing material, such as elastomeric material, which is secured to a portion of the wall of the housing over the port to serve as a flap covering the port. To close the valve, a finger or other object may be placed over the flap such that the elastomeric material is held sealingly in place. Alternatively, in the simplest form of this embodiment, as illustrated in FIG. 10, a finger may be used as the closure member to seal the port. The finger may be either bare or gloved with a material, for example, of the type typically worn in a laboratory, i.e., an elastomeric material such as latex or a similar material.

In operation, the valve may remain open during the time liquid is required to be maintained above the porous structure and closed prior to increasing the volume within the chamber. During the time that the valve is closed, the chamber is sealed to atmospheric pressure. If the chamber volume is increased during this time, liquid will be drawn through the porous structure. When the valve is next opened, the pressure within the chamber will be equilibrated with external pressure. Thus, the next liquid added to the space above the porous structure will tend to remain above the structure for whatever dwell or incubation time is required for optimum chemical interaction with the substances within or on the porous structure. With the valve in its open position such that there is communication between the chamber and the atmosphere, the volume of the chamber may be reduced, within the limits permitted by the volume of liquid in the chamber. Depending on the design of the valve, liquid may be removed from the chamber at this time through the valve. The valve may then be closed again and the chamber volume increased, resulting in any aliquot of liquid in the well above the porous structure being drawn through the porous structure. Alternatively, depending on the available free volume of the chamber and the volume of liquid in the chamber compared with the maximum volume of liquid that the chamber may be required to hold in a specific test procedure, after pressure is equilibrated, the two housing sections may be brought together and, where appropriate, the pressure release valve is then closed to again form a sealed chamber. With the valve closed, the two housing sections may then be separated again to increase the volume of the chamber and decrease the pressure. At the completion of the reaction(s) occurring on the outer surface of the porous structure (or other layer in intimate contact with the upstream surface of the porous structure), the surface of the porous structure is examined for, e.g., an optical indication of a positive reaction, such as a color change.

This valved embodiment of the present invention lends itself well to diagnostic assays which require multiple liquid dwell times (known as incubation steps), and makes possible assays which could not previously be accomplished without expensive and cumbersome equipment.

The device may also have an additional provision for removing some or all of the liquid in the chamber, either through the pressure release valve (as indicated above), a separate liquid release valve, or a pocket within the device for trapping liquid.

I claim:

1. A diagnostic device for testing at least one analyte in a liquid, the diagnostic device comprising:
    a housing having an exterior and including a chamber having one portion open to the exterior of the housing and another portion closed from the exterior of the housing:
    a porous structure disposed across the open portion of the chamber and hermetically sealed to the housing, the porous structure having a first surface communicating with the exterior of the housing, a second surface communicating with the closed portion of the chamber, and at least one layer which is wettable by a liquid:
    a valve in a wall of said housing; and
    means for increasing the volume of the closed portion of the chamber to thereby decrease the pressure within the closed portion of the chamber, the at least one wettable layer of the porous structure having a bubble point such that, when the wettable layer has been wetted by a liquid, the diagnostic device is capable of maintaining a pressure differential across the porous structure after the volume of the closed portion of the chamber has been increased by said volume increasing means to create a pressure differential across the porous structure.

2. The diagnostic device of claim 1 wherein said valve comprises a 2-way valve.

3. The diagnostic device of claim 1 wherein said valve comprises a 3-way valve.

4. The diagnostic device of claim 1 wherein said valve comprises a port in said housing extending between the exterior of said housing and said chamber and a movable closure member for obstructing said port.

5. The diagnostic device of claim 4 wherein said port includes a tube projecting outwardly from said housing.

6. The diagnostic device of claim 5 wherein said closure member includes a cap covering the projecting end of said tube.

7. The diagnostic device of claim 4 wherein said closure member comprises a plug.

8. The diagnostic device of claim 1 wherein said valve comprises a port extending between the exterior of said housing and said chamber, said port adapted to be closed by a closure member.

* * * * *